United States Patent [19]

Haff et al.

[11] Patent Number: 4,482,482

[45] Date of Patent: Nov. 13, 1984

[54] CESIUM TRIFLUOROACETATE SOLUTIONS FOR THE ISOLATION OF NUCLEIC ACIDS

[75] Inventors: Lawrence A. Haff, Sommerville, N.J.; Anthony J. Ewell, New York, N.Y.

[73] Assignee: Pharmacia, Inc., Piscataway, N.J.

[21] Appl. No.: 458,359

[22] Filed: Jan. 17, 1983

[51] Int. Cl.³ .................. C07G 7/00; C07H 17/00; C07H 19/00; C07H 21/00

[52] U.S. Cl. .................. 260/112 R; 436/542; 436/545; 436/547; 436/804; 536/22; 536/28; 536/29

[58] Field of Search .............. 260/112 R; 536/22, 28, 536/29; 436/542, 547, 545, 804

[56] References Cited

PUBLICATIONS

Nucleic Acids Research, 4819–4836 (1978), Burke et al.
Biopolymers–vol. 6, pp. 1325–1344 (1968), Tunis et al.
Biopolymers–vol. 10, pp. 1901–1924 (1971), Schmid et al.
Biopolymers–vol. 6, pp. 1345–1353 (1968), Tunis et al.
Analytical Biochemistry, 86, 264–270 (1978), Burke et al.

*Primary Examiner*—Howard E. Schain
*Attorney, Agent, or Firm*—Hubbell, Cohen, Stiefel & Gross

[57] ABSTRACT

A method for simultaneously isolating DNA, RNA and/or protein fractions from a crude biological mixture containing DNA, RNA and/or protein fractions is disclosed. The method comprises adding the crude biological mixture to an aqueous solution of cesium trifluoroacetate, the solution having a density from about 1.4 to about 1.6 g/ml, and centrifuging the resulting mixture under ultracentrifugation conditions.

13 Claims, 4 Drawing Figures ical mixtures. (As used herein,
CESIUM TRIFLUOROACETATE SOLUTIONS FOR THE ISOLATION OF NUCLEIC ACIDS

BACKGROUND OF THE INVENTION

This invention relates to a method of separating acids and/or proteins from a crude biological mixture. More particularly, this invention, in one of its embodiments, relates to a method of simultaneously separating nucleic acids and proteins from a crude biological mixture through the use of an aqueous salt solution of cesium trifluoroacetate.

In the fields of biochemistry, genetic engineering, molecular biology, medical research, and the like, it is often necessary to prepare pure samples of DNA and RNA from crude biological mixtures. (As used herein, the term "biological mixture" refers to a mixture of biological molecules, such as nucleic acids and proteins.) It is also important for workers in these fields to be able to isolate the DNA, RNA and protein fractions from crude biological mixtures. (As used herein, the term "protein" includes proteins as well as other polypeptides which may not be proteins.) Such crude biological mixtures are obtained when cells are lysed. The crude biological mixtures often contain low molecular weight compounds and carbohydrates as well as nucleic acids and proteins.

Heretofore, the technique known as "equilibrium density gradient centrifugation" has been used in the laboratory to isolate nucleic acids. In accordance with this technique, a crude or semi-purified biological mixture containing nucleic acids, proteins and other cellular components, is added to a dense salt solution and the resulting mixture is ultracentrifuged at very high gravity forces (e.g., 30,000 to 100,000 rpm) for periods of 1–3 days. Under the high centrifugal forces, the heavy salt ions are preferentially displaced outward, i.e., toward the bottom of the centrifuge vessel. A density gradient is thereby formed in the vessel with the liquid at the top of the vessel having a somewhat lower density than the liquid bottom of the vessel. Ideally, each of the biological molecules in the vessel will seek its own buoyant density and band in a different location. For example, DNA will normally band at a density in the neighborhood of about 1.5 g/ml.

The most commonly used salts for DNA purification by this technique are cesium chloride (CsCl) and cesium sulfate ($Cs_2SO_4$). These salts are sufficiently soluble in water to form solutions having a density of about 1.4–1.6 g/ml. Thus, these salts are adequate for isolating DNA from a crude biological mixture since DNA bands at about 1.5 g/ml. However, cesium chloride and cesium sulfate are inadequate for banding the RNA and protein fractions from a crude biological mixture. Due to the intense "salting-out" properties of the chloride and sulfate anions, proteins tend to precipitate from cesium chloride and cesium sulfate solutions and cannot be banded. In addition, the proteins which precipitate from solution cause some of the DNA to co-precipitate with them from solution. Therefore, crude mixtures must be thoroughly deproteinized before subjecting them to equilibrium density gradient ultracentrifugation in cesium chloride or cesium sulfate solutions.

Furthermore, RNA precipitates from and will not band in cesium chloride solution. While RNA will band in cesium sulfate solutions, RNA will precipitate out as well. Thus, neither cesium chloride nor cesium sulfate are satisfactory for simultaneously isolating DNA, RNA and protein fractions from crude or semi-purified biological mixtures.

Until recently, it has been necessary, in order to prepare pure samples of DNA by this technique, to free the DNA of protein by multiple extractions of the crude mixture with phenol or chloroform. It has also been necessary, in many cases, to treat the crude mixture with proteases in order to remove the proteins tightly bound to the DNA. It has also been necessary, in some cases, to treat the crude mixture with ribonuclease in order to degrade the RNA prior to its removal. These multiple treatments are time-consuming and inconvenient. The use of phenol is unpleasant and hazardous. The use of proteases and ribonuclease is fraught with difficulties because these enzymes can be easily contaminated with low levels of other enzymes.

Recently, aqueous solutions of cesium trichloroacetate ("CsTCA") have been proposed for the isolation of nucleic acids and proteins by the technique of equilibrium density gradient centrifugation. See Burke, R.L., and Bauer, W.R., 5 *Nucleic Acids Research*, 4819 (1978), and Burke, R.L., Anderson, P.J., and Bauer, W.R. 86 *Anal. Biochem.* 264 (1978). These publications disclose that various DNAs and RNAs can be banded in neutral CsTCA solutions without formation of any precipitate. However, cesium trichloroacetate solutions have not proved ideal for isolating nucleic acids and proteins because of three major limitations: (1) CsTCA solutions absorb strongly in the same region of the ultraviolet spectrum where nucleic acids also absorb strongly, thus hindering conventional techniques for detecting the presence of nucleic acids; (2) CsTCA slowly hydrolyzes in the presence of water to form chloroform and hydrochloric acid, thus hindering its use in solutions due to pH fluctuations and preventing its storage as a solution; and (3) upon occasion, dry CsTCA has been known to explode unexpectedly.

Thus, there remains a need for a method for isolating substantially pure fractions of DNA, RNA and/or proteins from a crude or semi-purified biological mixture without suffering the limitations presented by cesium trichloroacetate.

SUMMARY OF THE INVENTION

It has now surprisingly been found that this need for a method of isolating substantially pure fractions of DNA, RNA and proteins from a crude or semi-purified biological mixture can be met by a method of equilibrium density ultracentrifugation using dense aqueous solutions of cesium trifluoroacetate ("CsTFA").

The present invention, in one of its embodiments, embraces a method for isolating a nucleic acid from a biological mixture containing a nucleic acid, comprising adding the biological mixture to an aqueous solution of cesium trifluoroacetate, said solution having a density from about 1.4 to about 2.6 g/ml, and centrifuging the resulting mixture under ultracentrifugation conditions.

In another of its embodiments, the present invention embraces a method for simultaneously isolating substantially pure nucleic acid and protein fractions from a biological mixture containing nucleic acid and protein fractions, comprising adding the biological mixture to an aqueous solution of cesium trifluoroacetate, said aqueous solution having a density of from about 1.4 to about 2.6 g/ml, and centrifuging the resulting mixture under ultracentrifugation conditions.

By this newly discovered method, substantially pure fractions of DNA, RNA and/or proteins can be simultaneously isolated in soluble form from a crude or semipurified biological mixture. In addition, the aqueous solutions of CsTFA do not absorb strongly in the ultraviolet, are stable, and are not known to explode.

There have been some publications in the literature which disclose banding purified DNAs in CsTFA to obtain DNA hydration data (see Tunis, M.B., and Hearst, J.E., 6 Biopolymers 1325 (1968); Tunis, M.B., and Hearst, J.E., 6 Biopolymers, 1345 (1968); and Schmid, C.W., and Hearst, J.E., 10 Biopolymers 1901 (1971)). However, none of these publications discloses that aqueous solutions of CsTFA can be used with crude or semi-purified biological mixtures for isolating the DNA, RNA and/or protein fractions.

DETAILED DESCRIPTION OF THE INVENTION

Figure 1:
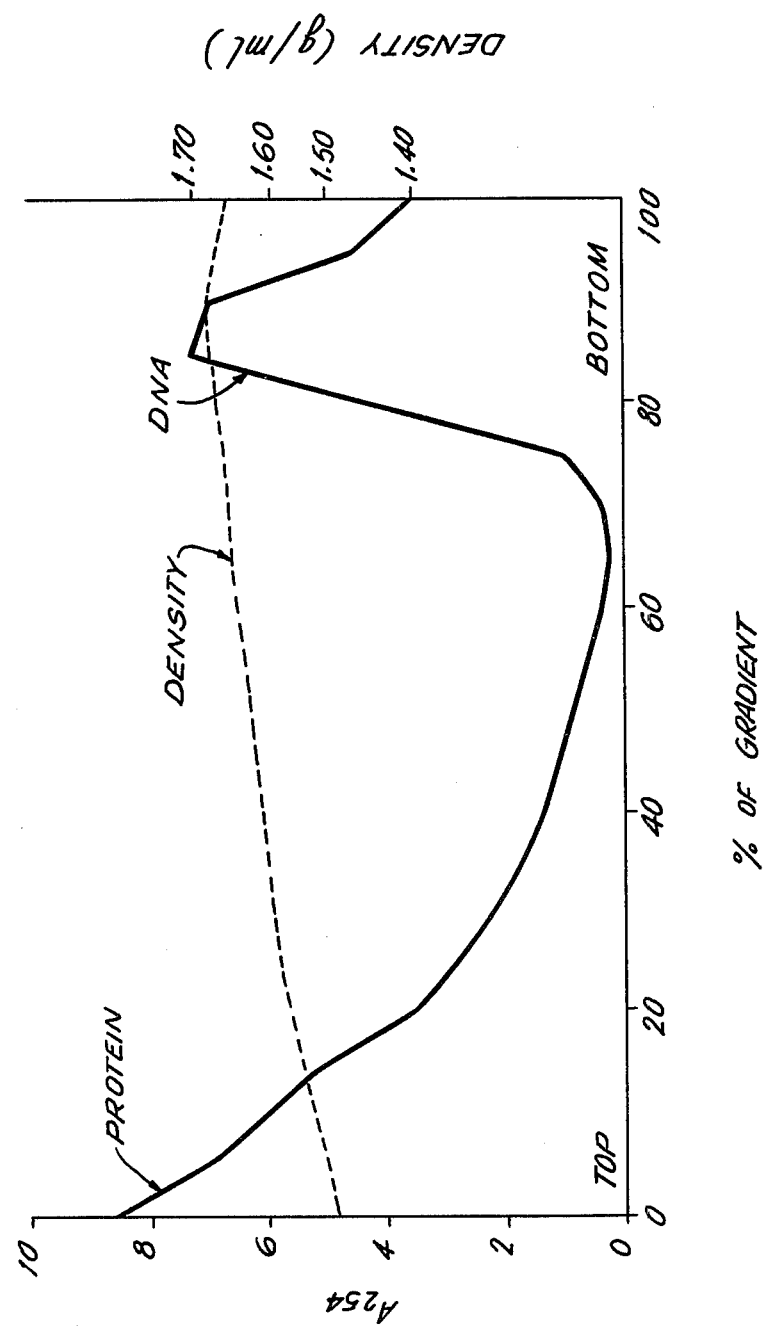
FIG. 1 illustrates banding of viral DNA according to the methods of the present invention.

In accordance with the present invention, it has now been found that substantially pure fractions of DNA, RNA and protein can be simultaneously banded in soluble form in aqueous solutions of cesium trifluoroacetate by the method of equilibrium density gradient ultracentrifugation. In carrying out the present invention, the CsTFA solution is used in the same manner as other salt solutions have been used in this technique.

In accordance with this method, a biological mixture containing DNA, RNA and/or protein is added to an aqueous solution of CsTFA having a density from about 1.4 to about 2.6 g/ml, preferably about 1.4 to about 2.0 g/ml, most preferably about 1.6 g/ml, in an ultracentrifuge tube, and then the resulting mixture is centrifuged at speeds of about 20,000–100,000 rpm for about 18–72 hours at a controlled temperature. The CsTFA solution should be buffered near neutrality with a conventional buffer at low concentration. In addition, the entire separation procedure, including centrifugation, should be done at temperatures of about 0° C.–25° C., preferably about 4° C.–20° C. After centrifugation, the contents of the tube are fractionated using standard techniques, and the fractions of interest, i.e., the purified fractions of DNA, RNA, and/or protein, are retained. The CsTFA can be separated from the DNA, RNA and protein fractions by conventional methods, e.g., by gel permeation chromatography, ethanol precipitation or dialysis.

In employing the method of the present invention, simultaneous banding of nucleic acids and proteins is achieved due to the unexpected properties of CsTFA in solution. Among these properties, the following may be mentioned:

(1) CsTFA is extremely soluble in water. Approximately 14 g of CsTFA will dissolve in 1 ml of water. CsTFA is also very soluble in other polar solvents, such as ethanol. The high solubility in polar solvents is believed to be due to the high polarity of the CsTFA molecule. Thus, cesium is the most electropositive element; trifluoroacetate is extremely electronegative due to the presence of three fluorine atoms at one end of the acetate radical.

(2) Aqueous solutions of CsTFA are extremely dense. This is due to the high solubility of CsTFA in water. A saturated solution of CsTFA has a density of about 2.6 g/ml. The high density of CsTFA is also believed to be due to the high density of both the cesium and trifluoroacetate ions.

(3) Because the TFA$^-$ ion promotes the hydration of other molecules, CsTFA is intensely solubilizing for other molecules. Thus, DNA, RNA, and protein are all soluble in CsTFA solutions.

(4) CsTFA solutions denature proteins. Thus, CsTFA is inhibitory to proteases and ribonuclease. CsTFA will also promote disaggregation of proteins from nucleic acids. CsTFA will cause even tightly bound protein to dissociate from DNA or RNA.

(5) CsTFA solutions will hydrate nucleic acids. As a result of this property, nucleic acids will band at a somewhat lower density in CsTFA solutions than in other salt solutions. Additionally, CsTFA solutions lower the melting point of nucleic acids.

While CsTFA solutions possess the above beneficial properties, CsTFA solutions do not possess the limitations of CsTCA. CsTFA solutions are much more transparent to ultraviolet light than CsTCA solutions; CsTFA solutions are much more stable than CsTCA solutions; CsTFA is not known to explode spontaneously. As a result of these properties, DNA, RNA and protein will all dissolve in CsTFA salt solutions having densities from about 1.4 to about 2.6 g/ml. When crude biological mixtures containing these biological materials are dissolved in CsTFA solutions and ultracentrifuged, the DNA will band at a density of about 1.4–1.6 g/ml, RNA will band at a density of about 1.6–2.0 g/ml, and protein will generally band at a density of about 1.2–1.5 g/ml. No deproteinization or removal of RNA from the crude biological mixture is required and no precipitation of RNA or protein occurs.

As examples of possible useful applications of the present invention, the following may be mentioned: the simultaneous separation and isolation of DNA, RNA, and protein from crude biological mixtures; the separation and isolation of different nucleic acids at different buoyant densities based upon different base compositions; the separation and isolation of single- and double-stranded DNA; the separation and isolation of DNA/RNA hybrids; the separation and isolation of nucleic acids covalently linked to proteins; the separation and isolation of ribosomal RNA; the separation and isolation of messenger RNA; the separation and isolation of DNA or RNA from a virus; the separation and isolation of nucleic acids from a cell or organelle; the separation and isolation of satellite DNA, such as plasmid DNA; the separation and isolation of circular, linear, nicked and looped DNA's (using ethidium bromide); the purification of radiolabelled DNA or RNA. The biological mixtures containing the aforementioned varieties of nucleic acids may be prepared by techniques well-known in the art.

It may further be mentioned that DNA and RNA can be extracted from a crude biological mixture in a simple one-step extraction procedure when the nucleic acids are not heavily burdened with protein. For example, viral DNA or RNA can be extracted and banded without the need for deproteinization.

CsTFA can be produced in the laboratory, for example, by titrating cesium carbonate ($Cs_2CO_3$) or cesium hydroxide (CsOH) with trifluoroacetic acid ($CF_3COOH$). This method has been disclosed in the publications cited above.

EXAMPLES

The following examples will serve to illustrate further the applications of the present invention:

Example 1: Isolation Of Viral DNA

An attempt was made to isolate DNA from lambda virus without resort to phenol extraction. 40 microliters of lambda virus was added to an aqueous solution of CsTFA (density of 1.69 g/ml) and centrifuged at 30,000 rpm for 43 hours at 18° C. After centrifugation, the ultraviolet absorbance at 254 nm and the densities throughout the gradient were determined. The results, shown in FIG. 1, indicate that the DNA banded at a density of 1.674 g/ml. (In the accompanying Figs., the density of a band is determined by reference to the dashed density line.)

In a second run, the same conditions were repeated except that this time the CsTFA solution also contained a small amount of sodium lauryl sarcosinate. This substance is a detergent which is soluble in CsTFA solutions, and which promotes dissociation of proteins from nucleic acids. The results of this second run, shown in FIG. 2, indicate that the DNA banded at a density of 1.612 g/ml.

Figure 2:
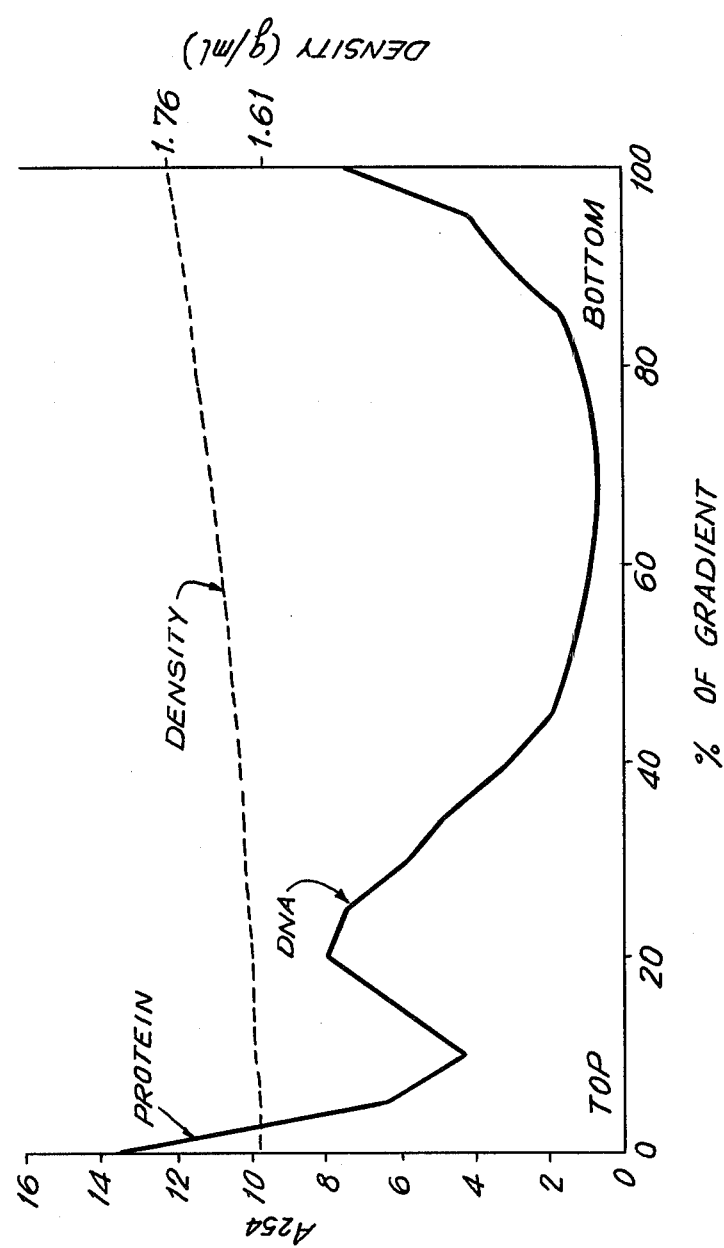
FIG. 2 also illustrates banding of viral DNA according to the methods of the present invention.

The results shown in FIGS. 1 and 2 indicate that viral DNA banded separately from contaminating protein. When the DNA fractions were combined and analyzed on silver-stained sodium dodecyl sulfate (SDS) electrophoresis gels, the DNA was found to be intact and free of contaminating protein. Thus, the CsTFA solutions can be used for the single-step isolation of viral DNA free of protein, without resorting to phenol extraction, and without causing damage to the DNA.

Example 2: Isolation Of Ribosomal RNA

Crude ribosomes were isolated from the livers of rabbits using techniques known in the art. 0.15 ml of a ribosomal suspension was added to 2 ml of an aqueous solution of CsTFA having a density of 1.5 g/ml. The solution was then added as a layer onto 2 ml of an aqueous solution of CsTFA having a density of 1.7 g/ml. (By this technique of layering, the time required to form the gradient is reduced.) The resulting mixture was then centrifuged at 30,000 rpm for 48 hours at 18° C. Following centrifugation, the mixture was fractionated using a Buchler "Auto-Density-Flow" apparatus and the densities were determined by refractive index.

Figure 3:
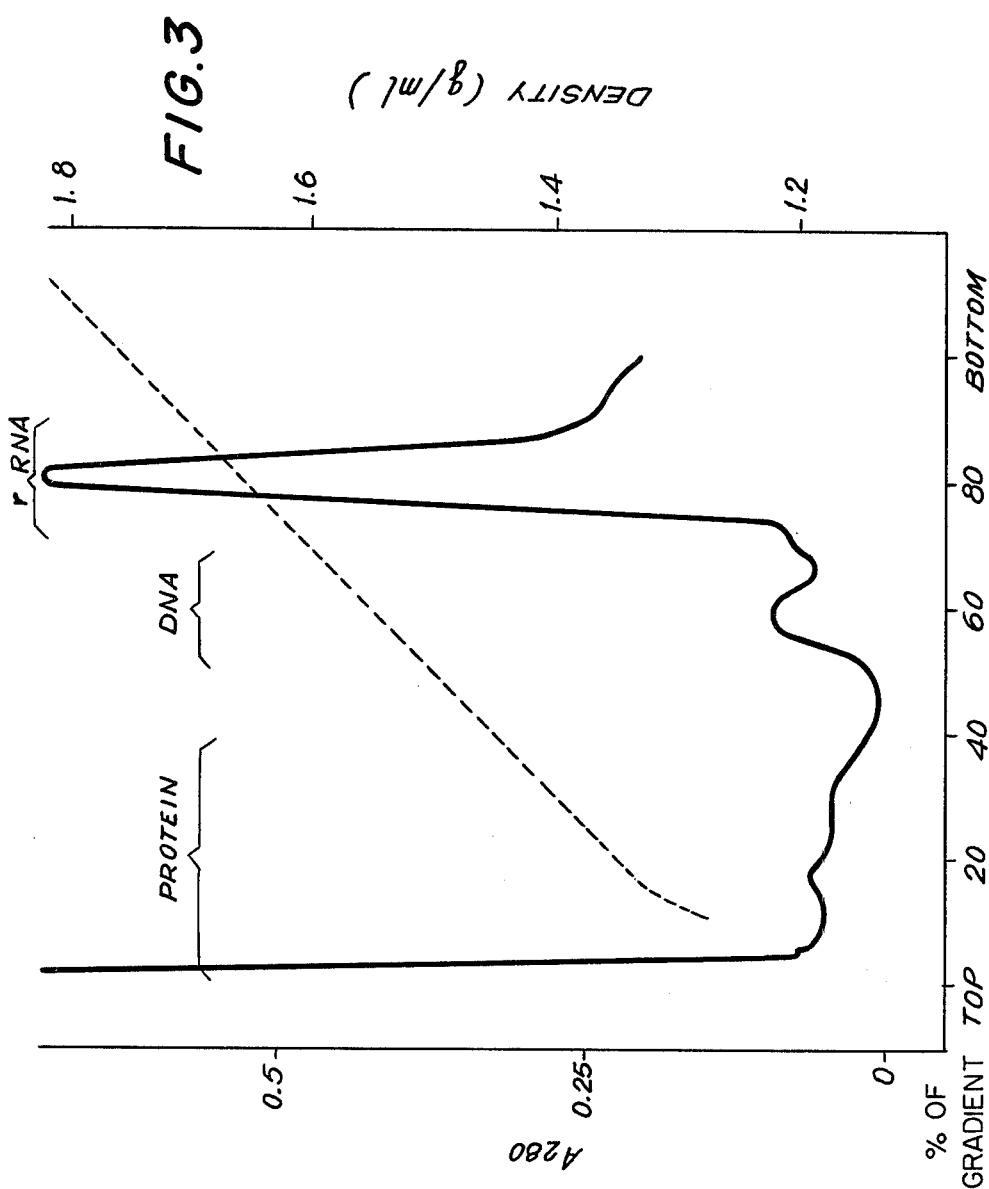
FIG. 3 illustrates simultaneous banding of DNA, RNA and protein obtained from crude rabbit liver ribosomes according to the methods of the present invention.

Typical results are shown in FIG. 3. Protein banded as a thin skin at the top of the centrifuge tube with a density less than 1.25 g/ml. A small amount of DNA banded at about 1.5 g/ml. The major peak of RNA banded at about 1.625 g/ml. There was no evidence of precipitation from any of the bands.

The RNA band was collected and analyzed by polyacrylamide gel electrophoresis. The analysis confirmed the presence intact of two major ribosomal RNA species, free of protein and DNA.

In a second run, all of the steps of the first run were repeated except that the initial ribosome/CsTFA solution (1.5 g/ml) was heated to 60° C. for 5 minutes prior to layering on the 1.7 g/ml CsTFA solution. The results were virtually identical to those of the first run.

In a third run, 0.5 ml of rabbit liver ribosomes were extracted using phenol-cresol-hydroxyquinilone and SDS to remove the protein. The RNA was precipitated in ethanol, dissolved in 2 ml of CsTFA solution (1.5 g/ml), layered onto 2 ml of CsTFA solution (1.7 g/ml), and centrifuged as described above. The phenol-extracted ribosomes produced a single sharp peak of RNA at the same density as the main peak of FIG. 3.

The results shown in FIG. 3 indicate that the present invention can be used to band DNA, RNA and protein simultaneously in a single centrifuge run and without precipitation occurring.

Example 3: Isolation Of Radiolabelled Rabbit Globin mRNA And Calf Thymus DNA Rabbit globin was collected and radiolabelled with tritium ($^3H$). The $^3H$- labelling was performed using dimethyl sulfate according to the method disclosed by Smith, et al, in 142 *Biochem. Biophys. Acta*, 323–330 (1967). A solution containing approximately 2 micrograms of $^3H$-labelled rabbit globin mRNA and 90 micrograms of calf thymus DNA was layered onto a 1.8 and 2.0 g/ml step gradient of CsTFA in a 5 ml polyallomer centrifuge tube and was spun at 30,000 for 90 hours at a temperature of 2° C. in a swinging bucket rotor. After centrifugation, the gradient was fractionated from the bottom by punching a hole in the tube and collecting fractions. The identity of the fractions was monitored by a scintillation counter for the $[^3H]$-mRNA and by a spectrophotometer at 260 nm for the DNA.

Figure 4:
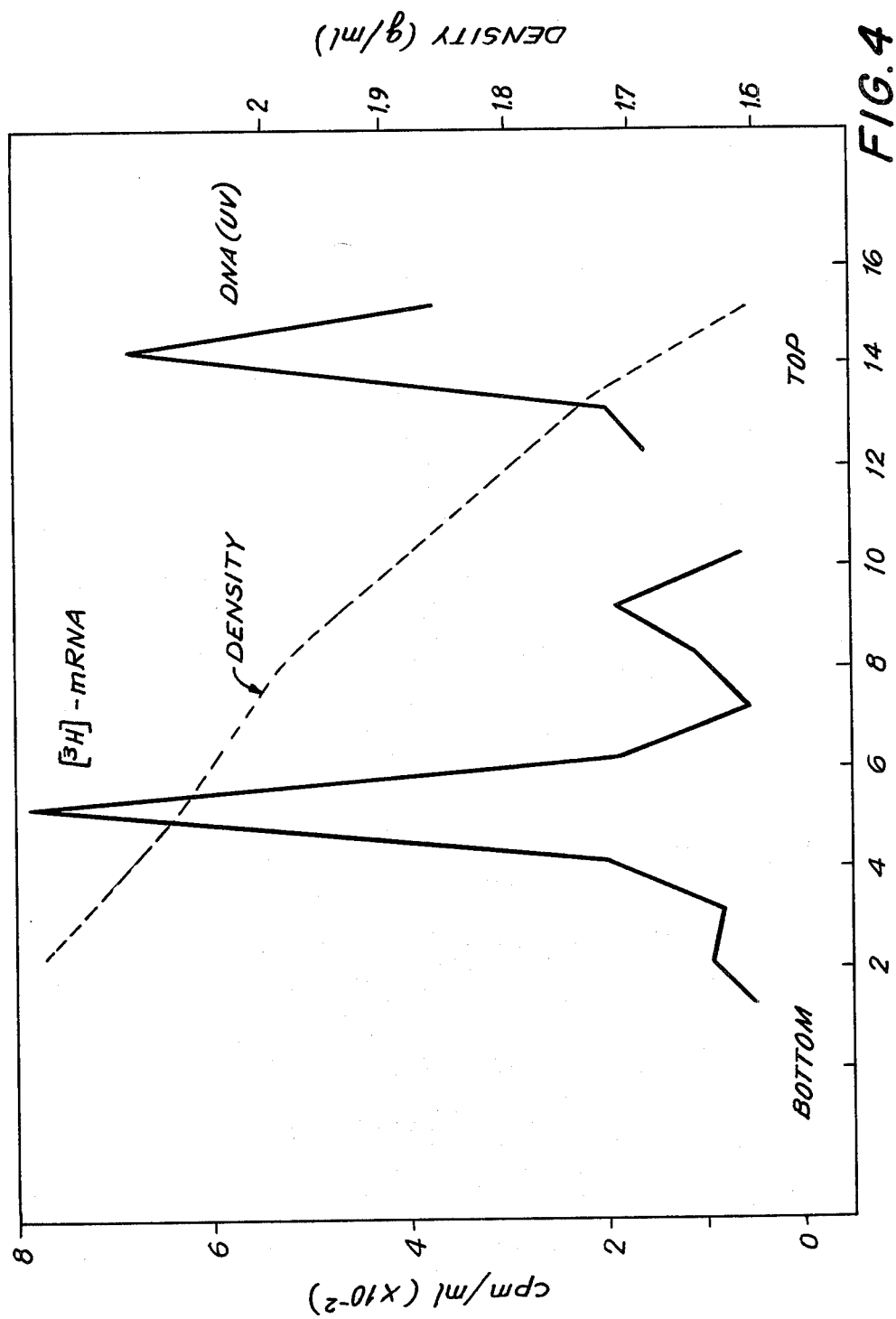
FIG. 4 illustrates simultaneous banding of radiolabelled rabbit globin RNA and calf thymus DNA according to the methods of the present invention.

The results are shown in FIG. 4 in which the bottom scale is the fraction number. These results demonstrate that substantially pure radiolabelled rabbit globin mRNA and calf thymus DNA can be banded simultaneously.

Example 4: Isolation of Circular and Linear DNA

A mixture of circular and linear DNA was extracted from lambda virus and was added to an aqueous solution of CsCl containing ethidium bromide. As is known in the art, ethidium bromide is a dye which binds to DNA complexes which are lower in density than free DNA. Ethidium bromide thus induces a difference in banding densities between circular, linear, supercoiled and nicked DNA since they bind different amounts of the dye.

When the mixture prepared as above was centrifuged at 40,000 rpm for 72 hours, the difference in banding densities was about 20–40 mg/ml. When the same experiment was repeated using an aqueous solution of CsTFA in accordance with the present invention, the difference in banding densities was about 50–100 mg/ml. The same result is obtained using plasmid DNA.

Example 5: Isolation Of Single- and Double-Stranded DNA

A crude mixture of double-stranded calf thymus DNA was prepared. In Run 1, the calf thymus DNA was added to an aqueous solution of CsCl (density 1.6 g/ml) and centrifuged at 40,000 rpm for 72 hours. The double-stranded DNA banded at about 1.6 g/ml. In Run 2, the same conditions were repeated except that the pH of the CsCl was adjusted to pH 11–12 by adding 0.1 M NaOH. The NaOH converts the double-stranded DNA into single-stranded DNA. This time, the single-stranded calf thymus DNA banded at about 1.65 g/ml, i.e., the single-stranded DNA banded at a density 50 mg/ml greater than the double-stranded DNA.

In Runs 3 and 4, the same conditions were repeated as in Runs 1 and 2 except that an aqueous solution of CsTFA was used in accordance with the present invention. In these runs, the single-stranded DNA banded at a density which was about 80–100 mg/ml greater than the double-stranded DNA.

While the invention has been described by reference to specific embodiments, this was for purposes of illustration only and should not be construed to limit the spirit or scope of the invention.

What is claimed is:

1. A method for isolating a nucleic acid and/or a protein fraction from a biological mixture containing a nucleic acid and/or a protein fraction, comprising adding the biological mixture to an aqueous solution of cesium trifluoroacetate, said solution having a density from about 1.4 to about 2.6 g/ml, and centrifuging the resulting mixture under ultracentrifugation conditions.

2. The method of claim 1 wherein said cesium trifluoroacetate solution has a density from about 1.4 to about 2.0 g/ml.

3. The method of claim 1, wherein said cesium trifluoroacetate has a density of about 1.6 g/ml.

4. The method of claim 1, 2 or 3 wherein said nucleic acid comprises DNA or RNA.

5. The method of claim 1, 2 or 3 wherein said nucleic acid comprises a single- or double-stranded nucleic acid.

6. The method of claim 1, 2 or 3 wherein said nucleic acid comprises a DNA/RNA hybrid.

7. The method of claim 1, 2 or 3 wherein said nucleic acid comprises messenger RNA or ribosomal DNA.

8. The method of claim 1, 2 or 3 wherein said nucleic acid comprises viral DNA, viral RNA or plasmid DNA.

9. The method of claim 1, 2 or 3 wherein said nucleic acid comprises circular, linear, nicked or looped DNA.

10. The method of claim 1, 2 or 3 wherein said nucleic acid comprises a satellite DNA.

11. The method of claim 1, 2 or 3 wherein said nucleic acid is covalently linked to proteins.

12. The method of claim 1, 2 or 3 wherein said biological mixture is obtained from cells or cell organelles.

13. The method of claim 1, 2 or 3 wherein said nucleic acid is radiolabelled.

* * * * *